United States Patent [19]

Davies

[11] Patent Number: 4,790,317

[45] Date of Patent: Dec. 13, 1988

[54] APPARATUS FOR RECOGNITION AND TERMINATION OF VENTRICULAR TACHYCARDIA AND VENTRICULAR FIBRILLATION

[76] Inventor: David W. Davies, St. Bartholomew's Hospital, London EC1, England

[21] Appl. No.: 923,408

[22] Filed: Oct. 27, 1986

[30] Foreign Application Priority Data

Oct. 25, 1985 [GB] United Kingdom ............... 8526417

[51] Int. Cl.⁴ .............................................. A61N 1/00
[52] U.S. Cl. ........................ 128/419 D; 128/419 PG
[58] Field of Search ..................... 128/419 D, 419 PG

[56] References Cited

U.S. PATENT DOCUMENTS 4,088,140 5/1978 Rockland et al. ............ 128/419 PG
4,384,585 5/1983 Zipes ................................ 128/419 D
4,427,011 1/1984 Spurrell et al. ................. 128/419 D
4,473,078 9/1984 Angel ............................. 128/419 D
4,475,551 10/1984 Langer et al. .................. 128/419 D Primary Examiner—Francis Jaworski
Assistant Examiner—George Manuel

[57] ABSTRACT

For automatic recognition of ventricular tachycardia and ventricular fibrillation, pulse sequences are compared which are obtained when sensing at at least one position on each ventricular epicardial surface of a heart. Changes in the sequence of activations and in the timing from pulsing at one sensor position to a next pulsing at that same position will indicate both ventricular tachycardia and ventricular fibrillation so as to enable a response to be made to restore a pulse sequence representing normal ventricular activity of the heart.

18 Claims, 7 Drawing Sheets

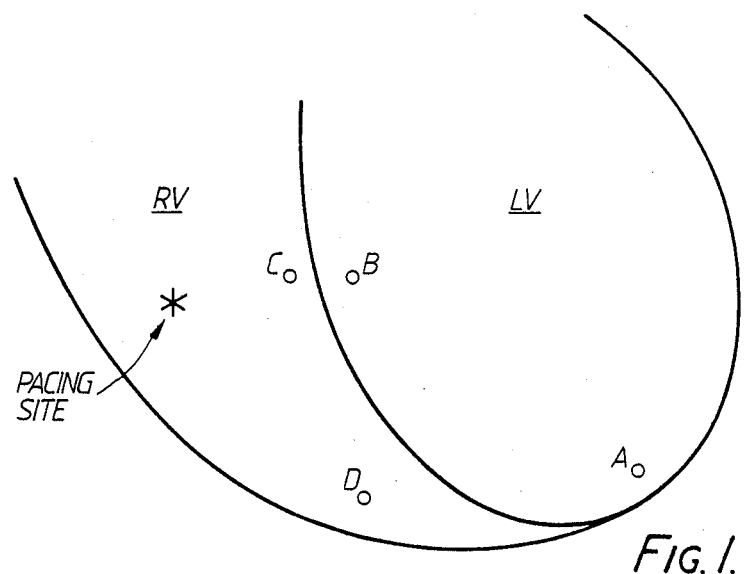
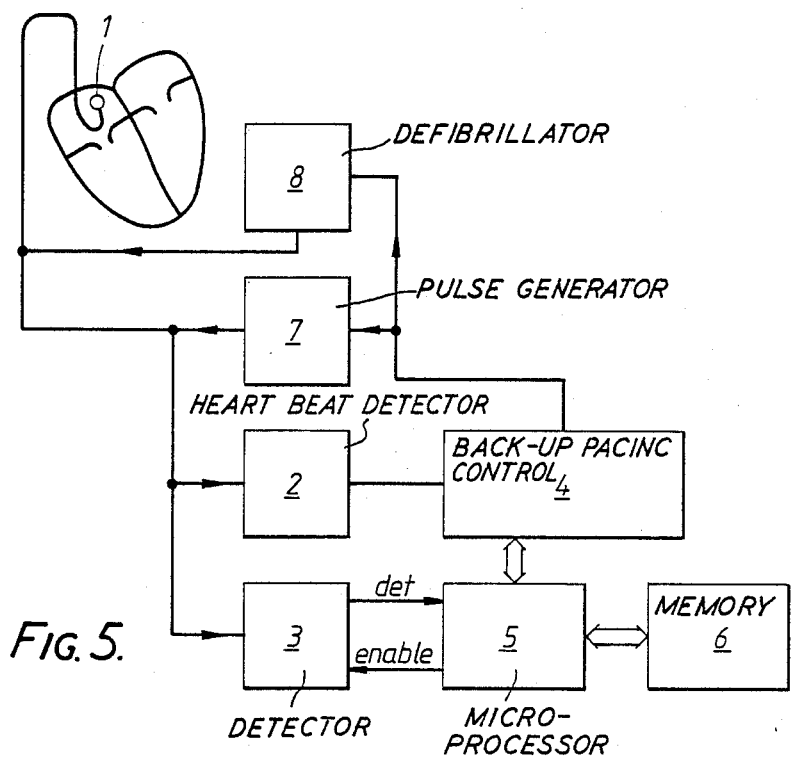

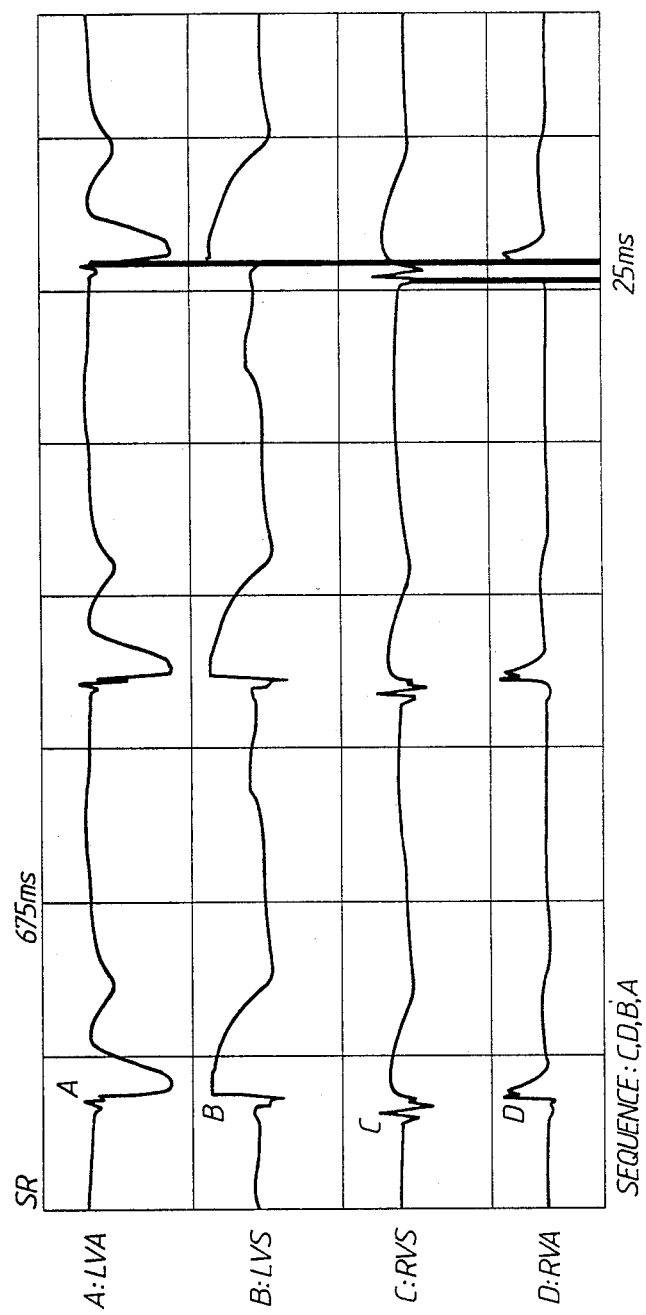

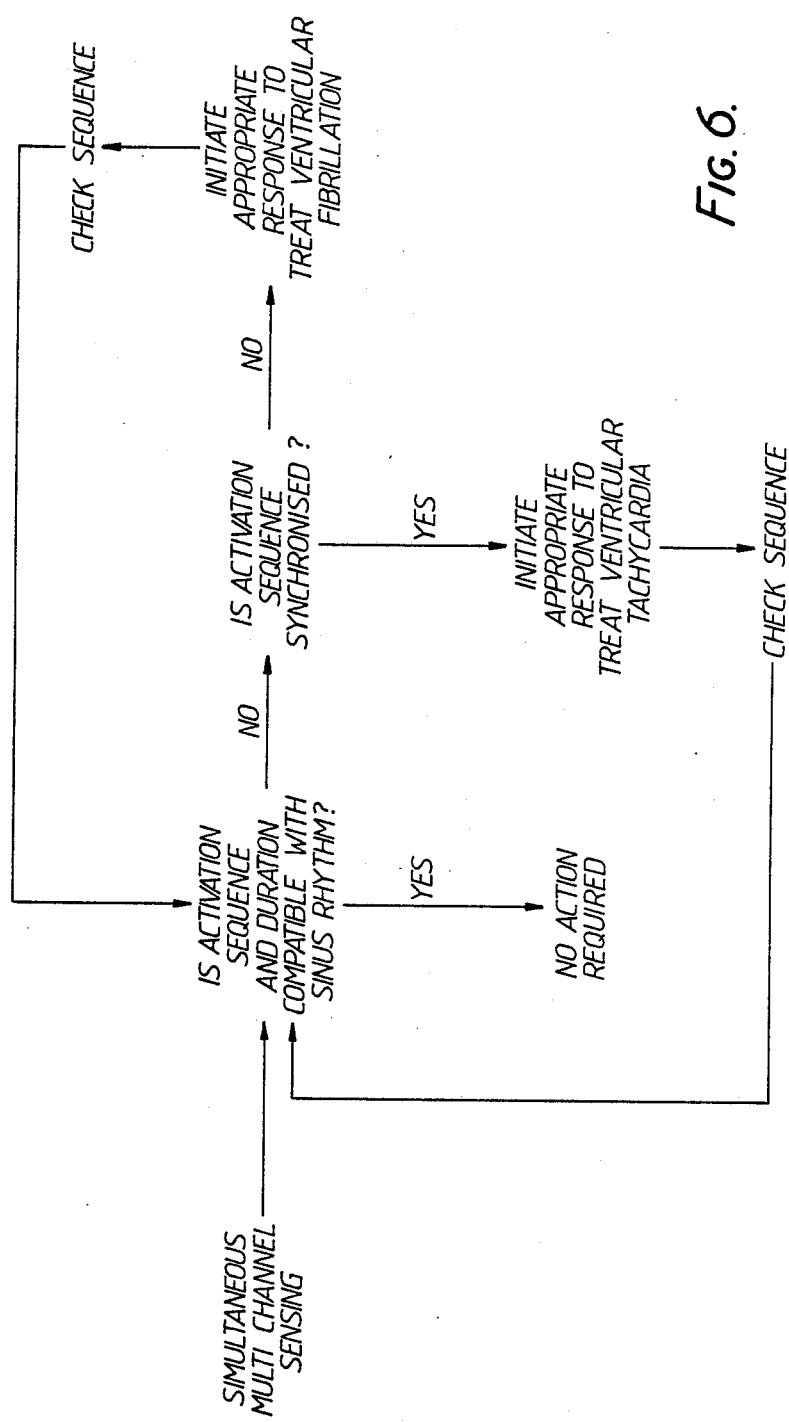

APPARATUS FOR RECOGNITION AND TERMINATION OF VENTRICULAR TACHYCARDIA AND VENTRICULAR FIBRILLATION

BACKGROUND OF THE INVENTION

This invention relates to apparatus for recognition of ventricular tachycardia and ventricular fibrillation from epicardial electrogram timings, and for termination thereof.

Ventricular fibrillation is defined as a condition characterized by fibrillary electrical activity of the ventricular muscle, the electrical impulses traversing the ventricles so rapidly that coordinated contractions cannot occur. This must be distinguished from ventricular tachycardia which may be defined as a rapid (greater than 100 beats per min.) cardiac rhythm originating in the ventricles. If sustained, it is usually synchronized in terms of overall ventricular contraction. Both should be differentiated from the normal situation of sinus rhythm where the heart's rhythm is controlled by depolarization originating from the sinus node and which spread sequentially through the atria, the AV node, the His-Purkinje system, and ventricular myocardium.

SUMMARY OF THE INVENTION

It is an object of the invention to provide an apparatus for recognizing both ventricular tachycardia and ventricular fibrillation, and means for responding to both these conditions to restore normal heart rhythm.

According to the present invention, an apparatus is provided for the automatic recognition of ventricular tachycardia and ventricular fibrillation. At least two sensors are provided, one sensor being attached at least to each ventricular epicardial surface of a heart. Signal paths connect the sensors to programmed means for detecting a pulse sequence representing the ventricular electrical activity of the heart and for comparing the pulse sequence detected with that representing the electrical activity of the heart during normal ventricular rhythm of the heart. Means are provided for converting the detected pulse sequence into a form which will be useful for providing a corrective response to a pulse sequence representing the electrical activity of the heart during abnormal ventricular rhythm of the heart. The apparatus is generally used in association with means for supplying to the heart stimuli to restore normal rhythm to the heart following detection of abnormal ventricular rhythm. In such a case there may be no need for converting the detected pulse sequence into a readable form or other form, such as audible form, which permits identification of a pulse sequence representing electrical activity of the heart during abnormal ventricular rhythm.

BRIEF DESCRIPTION OF THE DRAWINGS

FIG. 1 shows schematically an arrangement of four ventricular activation sites;

FIG. 2 shows the electrograms obtained from the four sites during normal sinus rhythm;

FIG. 5 is a block diagram of a cardiac implant embodying this invention; and

FIG. 6 is a flow chart indicating the characteristic operation of the present invention.

DESCRIPTION OF THE PREFERRED EMBODIMENTS

The feasibility of automatic recognition of ventricular tachycardia and ventricular fibrillation has been examined in a number of patients undergoing coronary artery surgery. Bipolar epicardial electrograms from four discrete points on the surface of the heart have been recorded during operation. The points are indicated on the ventricles of the heart. It has been observed that during normal rhythm, the points which are recorded are activated in a certain sequence which is at least consistent, although not always specific to that rhythm. Thus, referring to FIG. 1 of the accompanying drawings, the locations of four discrete points numbered A, B, C, and D on the left ventricle (LV) and right ventricle (RV) are shown, two of the points (A and D) being on the left ventricular and right ventricular apices, and points B and C being at left ventricular and right ventricular paraseptal positions. A pacing site is located on the right ventricle adjacent the third point. During normal rhythm, activation took place in the sequence C, D, B, A in this particular case (see FIG. 2). Furthermore, the timing from the first detected deflection to the last of the four was always the same during normal rhythm, and in this example, because of normal rhythm, the timing is short, and is of the order of 25 msec.

With abnormal rhythm, this timing will generally be increased and the sequence of activations changed.

Figure 3A:
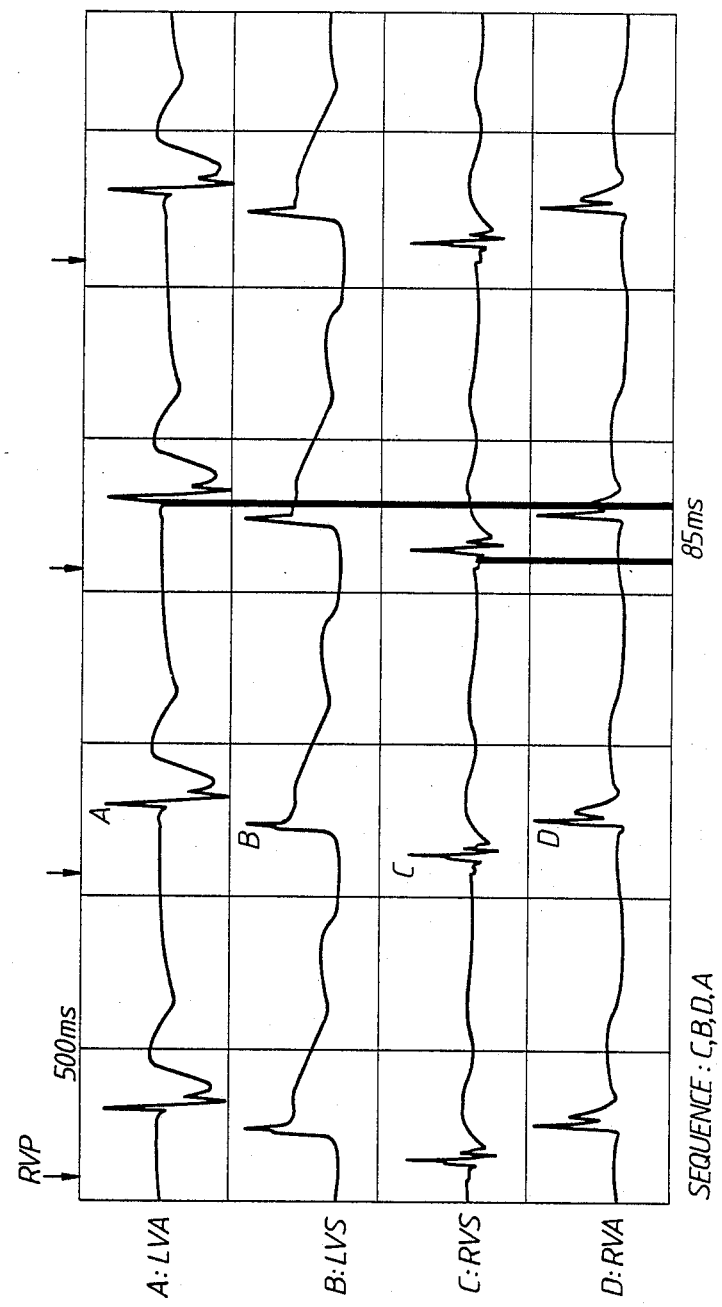
FIGS. 3A, B, and C show electrograms obtained under simulated ventricular tachycardia conditions.
Figure 3B:
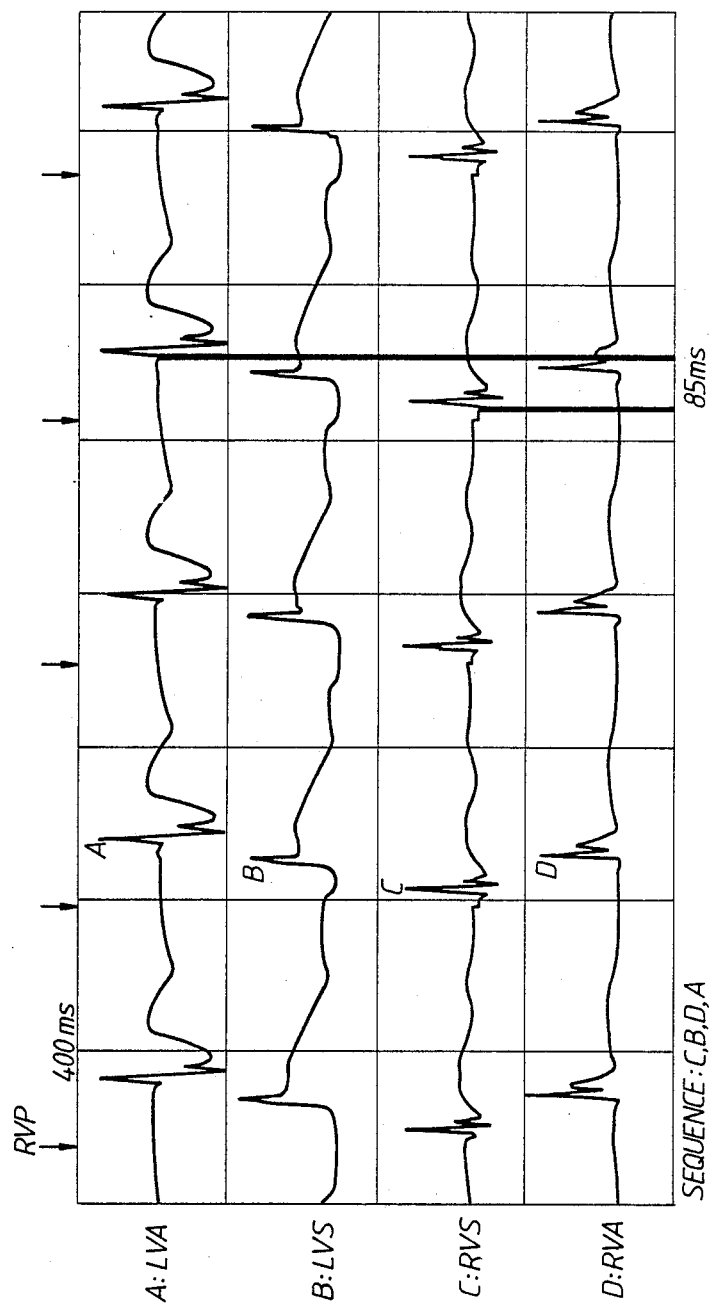
Figure 3C:
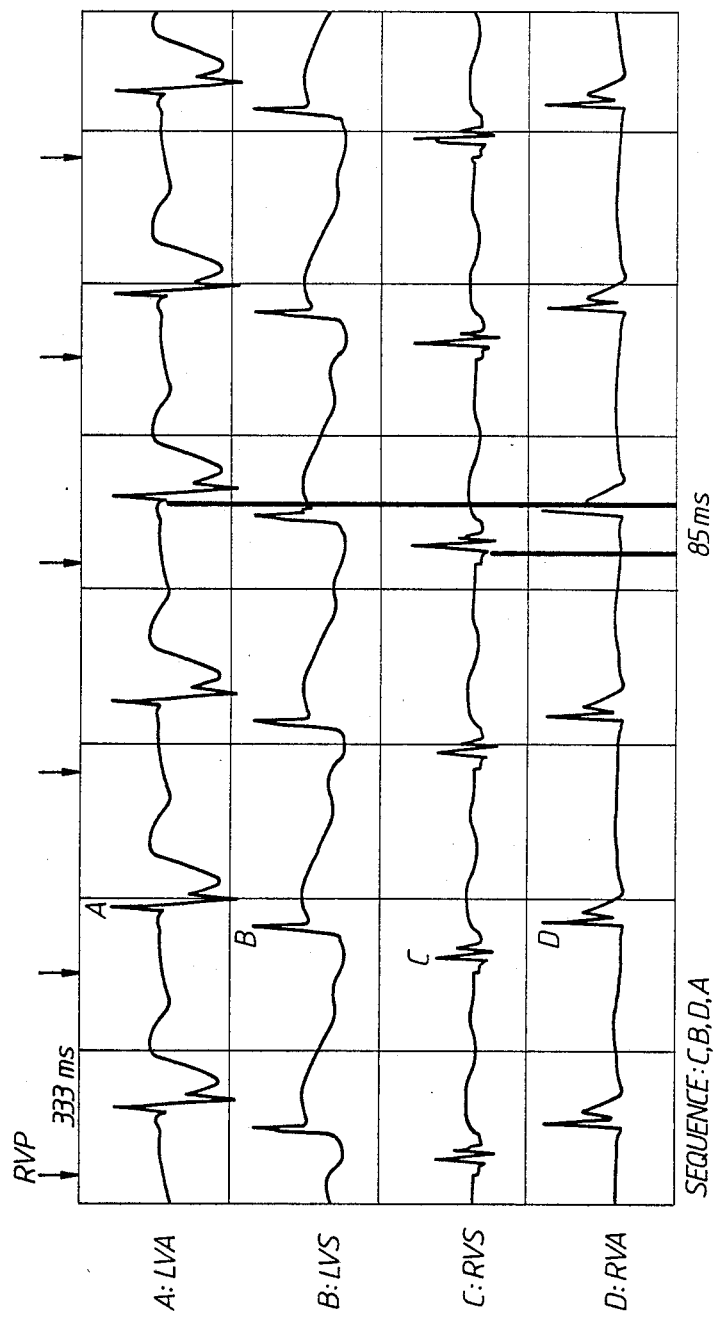
Figure 4:
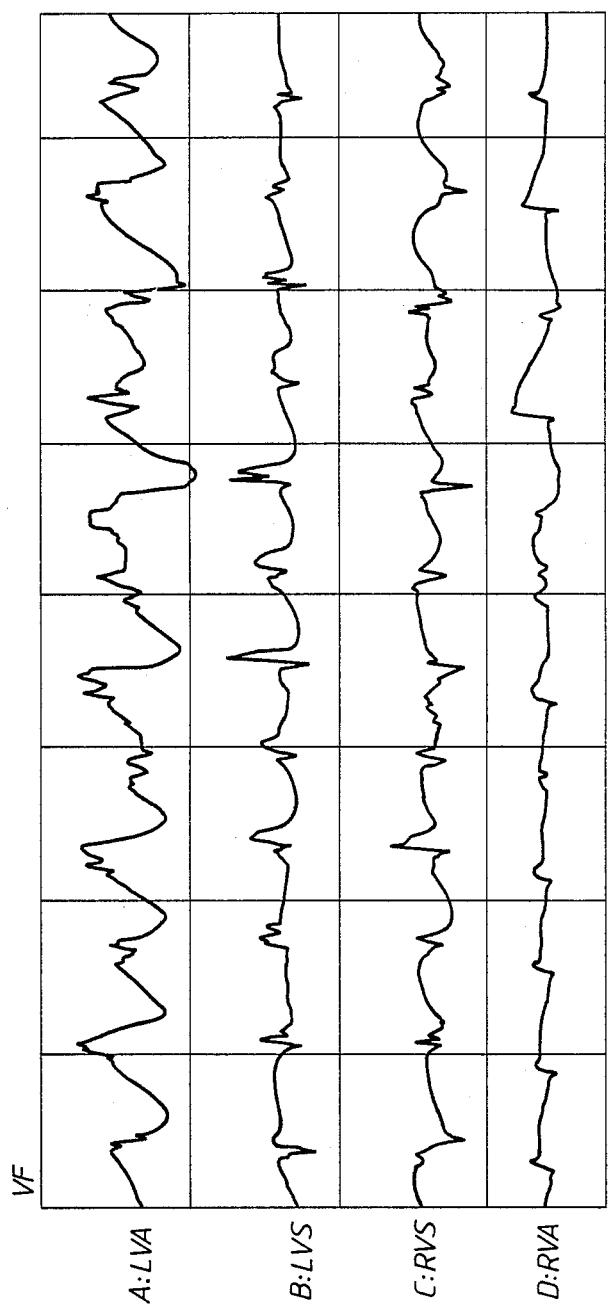
FIG. 4 shows the electrograms obtained at the four sites under conditions of ventricular fibrillation.

This latter observation was established by simulation of an abnormal rhythm by pacing from the site on the right ventricle. It was observed that 8 out of a group of 10 patients paced at this particular site showed a change of sequence of activation compared with that seen during normal sinus rhythm. Recording of the sequences obtained showed that activations change from C, D, B, A to C, B, D, A. Another abnormality which was induced (because a normal conducting system was not used) was that the spread of activity took longer across the heart. Thus, the timing from the onset of depolarization detected first at site C and finally at site A took 85 msecs, as opposed to 25 msecs. FIGS. 3A, 3B, and 3C indicate that this duration and sequence of activation is not affected by the rate of the abnormal rhythm, provided that its site of origin remains constant.

While maintaining the same set of sites, further experimentation to induce ventricular fibrillation yielded further results of interest. Ventricular fibrillation was induced by putting AC current onto a heart under cardiopulmonary by-pass (this is a means of obtaining cardiac arrest and is often used during surgery). It was observed that during ventricular fibrillation, the electrical activity at all four sites was extremely rapid, and certainly more rapid than normally seen. However, there was no apparent fixed sequence of activation. The activity can therefore be described as asynchronous. Because of the asynchronous nature of activity, there can be no fixed duration of activity. Thus, this provides a means of using multi site testing to distinguish between ventricular tachycardia (where there is likely to be an altered sequence of depolarization compared with normal rhythm and an increased duration of activation over that occurring during normal sinus rhythm) and ventricular fibrillation when all this synchrony is lost and the electrical activity from different points in the heart becomes asynchronous.

The apparatus of the present invention is programmed to respond to ventricular tachycardia or ventricular fibrillation when they are observed based upon an altered sequence and duration of ventricular activation as detected by impulses sensed from the epicardial sensing sites.

The present invention is of particular value since ventricular fibrillation has so far been a very difficult rhythm to detect reliably in automatic fashion. Moreover, the energy required by an implantable device to treat ventricular fibrillation is likely to be higher than that required to treat ventricular tachycardia. Therefore, by the use of this technique, lower energies can be selected for termination of ventricular tachycardia, thus prolonging battery life. There is thus provided a reliable method for the first time of detecting ventricular fibrillation. The micro-computer utilized in the circuit for comparing the activation sequence with that during sinus rhythm can then control a defibrillator which can be discharged when a rhythm characteristic of ventricular fibrillation or ventricular tachycardia is detected. Appropriate software is provided for controlling the micro-computer.

FIGS. 5 and 6 show practical embodiments of the invention and should be viewed in conjunction with each other. Thus, an implant 1 (sensors are not shown in FIG. 5 but are preferably at positions such as shown in FIG. 1) will monitor heart beat rate at all times using a normal heart beat detector 2 having a time base and backup pacing control 4 whose operation is directed by a microprocessor 5 having a memory 6. Should a high heart rate be detected, then a detector 3 which is normally operating in backup mode is switched on and simultaneous multichannel sensing is carried out (FIG. 1 shows sensing at four sites being carried out). This number is adequate in general, and there is no reason why more or less than four sites may be used for testing, although the use of four sites has been found to be an optimum compromise between cost and sensitivity. The microcomputer 5 which is utilized with the detector and receives signals therefrom will check by means of memory 6 whether activation sequence and duration are compatible with sinus rhythm. If this is the case, then no action will be required. However, if the activation sequence and duration are not compatible with sinus rhythm, then provided that an activation sequence is synchronized indicating ventricular tachycardia, a response appropriate to treatment of ventricular tachycardia will be initiated, i.e. stimuli will be delivered by pulse generator 7. In certain cases which depend on the type of tachycardia, however, ventricular tachycardia may be located by a relatively low energy shock for an associated defibrillator 8. If the activation sequence is not synchronized, indicating that ventricular fibrillation is taking place, then operation of the defibrillator 8 will take place.

In the preferred embodiment of the invention and again referring to FIG. 5, the normal heartbeat detector employs a band pass filter which receives the heartbeat signal and connects it to a first input of a threshold comparator whose other input is connected to a reference. The detector 3 is a Tachy detector which is morphology sensitive. The time base and back-up pacer control 4 is the known control logic of the pace function and can be over-ridden by the microcomputer or microprocessor 5. The microprocessor is preferably formed of the Intel 8085 microprocessor chip and the memory 6 is a ROM memory, Intel 27C64. The defibrillator stage 8 generates stimulation pulses in known prior art fashion and such a typical stage is shown in U.S. Pat. No. 4,321,928.

Although various minor changes and modifications may be proposed by those skilled in the art, it will be understood that I wish to include within the claims of the patent warranted hereon all such changes and modifications as reasonably come within my contribution to the art.

I claim as my invention:

1. A system for automatic recognition of either ventricular tachycardia or ventricular fibrillation of a heart, comprising:
   at least a first sensor connected to a left ventricle at a cardial surface thereof and at least a second sensor attached to a right ventricle at a cardial surface thereof;
   first means for detecting first and second respective pulse sequences derived from signals from the first and second sensors and determining whether activation sequence and time duration between detection of onset of depolarization for the two pulse sequences compared to each other indicate acceptable sinus rhythm;
   second means for treating ventricular fibrillation;
   third means for treating ventricular tachycardia; and
   fourth means connected to the first means for identifying and distinguishing between ventricular fibrillation and ventricular tachycardia by detection of a lack of synchrony of the activation sequence, and for activating the third means to treat ventricular fibrillation when such treatment is identified and for activating said fourth means when ventricular tachycardia is identified.

2. A system according to claim 1 wherein the first and a third sensor are provided on the left ventricle epicardial surface and the second and a fourth sensor are provided on the right ventricle epicardial surface and said first means detects first through fourth pulse sequences derived from signals from the first through fourth sensors, and the first means checking the time duration and activation sequence with respect to all four pulse sequences.

3. A method for detecting ventricular fibrillation, comprising the steps of:
   providing at least a first sensor at a first location of a heart and providing at least a second sensor at a second different location of the heart;
   sensing for ventricular fibrillation as a result of a loss of synchrony of activation in respective pulse sequences from the two sensors relative to each other; and
   activating a defibrillator when ventricular fibrillation is sensed.

4. A method according to claim 3 wherein the first and a third sensor are provided on the left ventricular epicardial surface and the second and a fourth sensor are provided on a right ventrical epicardial surface and synchrony as to all four pulse sequences is sensed.

5. A method according to claim 4 wherein the first and second sensors are provided at the respective left ventricle and right ventricle and third the fourth sensors are respectively provided at the left ventricle and right ventricle positions.

6. A system for detecting ventricular fibrillation, comprising:

at least a first sensor means for placement at a first location of a heart and at least a second sensor means for placement at a second different location of the heart;

first means connected to the first and second sensor means for producing first and second respective pulse sequences corresponding to signals from the first and second sensors;

second means connected to the first means for sensing ventricular fibrillation as a result of a loss of synchrony of activation between the first and second pulse sequences from the two sensor means relative to each other; and means for activating a defibrillator when ventricular fibrillation is detected by said second means for sensing ventricular fibrillation.

7. An apparatus for automatic recognition of ventricular tachycardia or ventricular fibrillation as distinguished from normal rhythm of a heart, comprising:

a first sensor means adapted to be placed at a first location of the heart for detecting an electrical signal from said first location of the heart;

at least a second sensor means adapted to be placed at a second location of the heart for detecting electrical signal from detecting an second location of the heart;

detecting means electrically connected to said first and second sensor means for creating first and second pulse sequences each of which represents electrical activity of the heart at the respective first and second locations; and rhythm abnormality detection means electrically connected to the detecting means for distinguishing ventricular tachycardia from normal rhythm by sensing for a change in sequence of activation between the at least first and second pulse sequences, and for distinguishing ventricular fibrillation from ventricular tachycardia through loss of synchrony in the sequence of activation between the first and second pulse sequences.

8. An apparatus according to claim 7 wherein said rhythm abnormality detection means also senses a spread of activity across the heart between the first and second locations by determining a time duration between detection of onset of depolarization at the first and second locations, and if an increase of the time duration occurs compared to a time duration of normal rhythm, then the detection means identifies an abnormal rhythm compared to a normal rhythm.

9. An apparatus according to claim 7 wherein third and fourth sensor means are also provided at respective third and fourth locations of the heart, said detecting means also produces third and fourth respective pulse sequences, and said abnormality detecting means compares a sequence of activation of the first through fourth pulse sequences.

10. An apparatus according to claim 7 wherein the first sensor means attaches to a left ventricular epicardial surface of the heart, and the second sensor means attaches to a right ventricular epicardial surface of the heart.

11. An apparatus according to claim 7 including ventricular tachycardia treatment means and ventricular fibrillation treatment means being connected to said rhythm abnormality detecting means, said rhythm abnormality detecting means activating either said ventricular tachycardia treatment means or said ventricular fibrillation means depending upon a type of treatment recognized.

12. A method for automatic recognition of ventricular tachycardia and ventricular fibrillation as distinguished from normal rhythm of a heart, comprising steps of:

sensing heart electrical activity at first and second separate locations of the heart;

determining abnormal ventricular rhythm by sensing for a change in sequence of activation of the first and second pulse sequences derived from the first and second locations sensed on the heart; and distinguishing between ventricular tachycardia and ventricular fibrillation by sensing for a loss of synchrony in the sequence of activation between the pulse sequences.

13. A method according to claim 12 including the steps of: in addition to sensing for a change of sequence of activation, also sensing for a spread of activity across the heart between the first and second locations by detecting a timing duration from onset of depolarization at one of the two locations as compared to onset of depolarization at the other location by comparison of the pulse sequences to one another, and if an increase in said time duration is determined, then an abnormal rhythm is recognized.

14. A method according to claim 12 including the steps of selecting the first and second locations of the heart such that a change in pulse sequence will result when either ventricular tachycardia or ventricular fibrillation occurs as compared to normal rhythm.

15. A method according to claim 12 wherein a rate of each of the pulse sequences is detected, and when a higher than normal rate occurs as compared to normal rhythm, then the change of sequence of activation is sensed for.

16. An apparatus for recognition and treatment of ventricular tachycardia and ventricular fibrillation, comprising:

a plurality of sensor means at respective plural locations of a heart;

means for creating a plurality of pulse sequences based on signals received from the plurality of sensor means;

heartbeat detector means for determining a heartbeat rate of the plurality of pulse sequences;

activation sequence detector means also connected to the plurality of sensor means for detecting a change in sequence of activation of the plurality of pulse sequences relative to one another as a result of a change from normal heart rhythm to an abnormal rhythm indicative of either ventricular tachycardia or ventricular fibrillation, and for detecting a loss of synchrony of sequence of activation of the plurality of pulse sequences relative to each other indicative of ventricular fibrillation;

ventricular fibrillation treatment means activated by the abnormality detector means when ventricular tachycardia is recognized; and ventricular fibrillation treatment means connected to the activation sequence detector means when ventricular fibrillation is indicated.

17. An apparatus according to claim 16 wherein the activation sequence detector means only checks for a change of activation sequence when the heartbeat detector means detects an abnormally high heartrate.

18. An apparatus according to claim 16 wherein said activation sequence detector means further detects for a spread of activity across the heart between the first and second locations by checking a time duration of onset of depolarization detected at one of the two locations as compared to onset of depolarization at the other location, and if an increase in such time duration occurs, an abnormal rhythm is detected.

* * * * *

UNITED STATES PATENT AND TRADEMARK OFFICE
CERTIFICATE OF CORRECTION

PATENT NO. : 4,790,317
DATED : December 13, 1988
INVENTOR(S) : David W. Davies

It is certified that error appears in the above—identified patent and that said Letters Patent is hereby corrected as shown below:

```
Claim 1, column 4, line 33, change "third" to --second--;
     line 35, change "fourth" to --third--.
```

Signed and Sealed this

Fourth Day of July, 1989

Attest:

DONALD J. QUIGG

Attesting Officer

Commissioner of Patents and Trademarks